United States Patent [19]

Bilitewski et al.

[11] Patent Number: 5,770,439
[45] Date of Patent: Jun. 23, 1998

[54] THICK-FILM CONDUCTIVITY ENZYME ELECTRODES IN A VERTICAL STACK AS BIOSENSOR

[75] Inventors: Ursula Bilitewski; Wiebke Drewes, both of Braunschweig; Franz Bechtold, Cadolzburg, all of Germany

[73] Assignee: Gesellschaft fur Biotechnologische Forschung mbB (GBF), Braunschweig, Germany

[21] Appl. No.: 952,044

[22] Filed: Sep. 28, 1992

[30] Foreign Application Priority Data

Sep. 28, 1991 [DE] Germany .......................... 41 32 441.2

[51] Int. Cl.$^6$ .......................... C12M 1/40; G01N 27/327; G01N 11/00; G01N 11/14
[52] U.S. Cl. .................. 435/287.1; 204/403; 435/174; 435/176; 435/177; 435/180; 435/817
[58] Field of Search .................................. 435/174, 176, 435/177, 180, 817; 204/403

[56] References Cited

U.S. PATENT DOCUMENTS 4,721,601  1/1988  Wrigton et al. ........................ 422/68
5,063,081  11/1991  Cozzette et al. ..................... 204/403 X

FOREIGN PATENT DOCUMENTS 4013593  10/1991  Germany .

OTHER PUBLICATIONS

Takatsu, et. al., Sensor and Activators, 11 (1987) pp. 309–317.

*Primary Examiner*—David M. Naff
*Attorney, Agent, or Firm*—Kane, Dalsimer, Sullivan, Kurucz, Levy, Eisele and Richard

[57] ABSTRACT

A biosensor is produced by depositing thick film pastes by screen-printing on a substrate to produce thick-film conductivity electrodes, and immobilizing enzymes on the electrodes. In specific embodiments, the substrate is an unfired ceramic, a fired ceramic or a plastic, the paste is a noble metal paste, enzyme immobilization is with a bifunctional reagent, a plurality of different enzymes are immobilized on different electrodes, and/or the electrodes are printed as parallel lines or in the image of a comb or concentric circles. A multi-dimensional biosensor is prepared by forming thick film paste electrodes containing an immobilized enzyme on a plurality of separate substrates, disposing the separate substrates one on top of the other in a vertical stack, pressing the stacked substrates together and curing the paste.

14 Claims, 4 Drawing Sheets

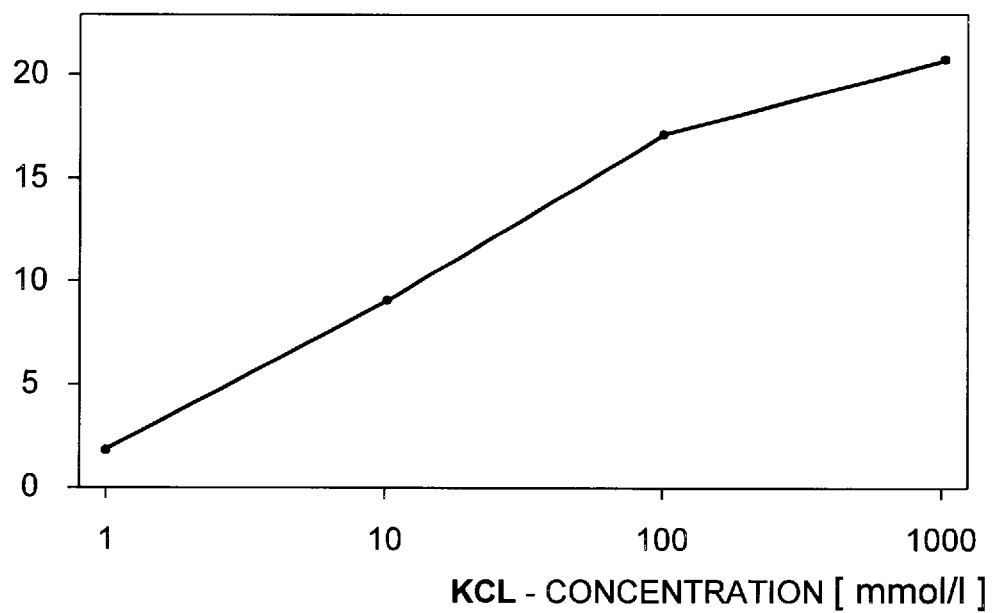
F I G. 5A
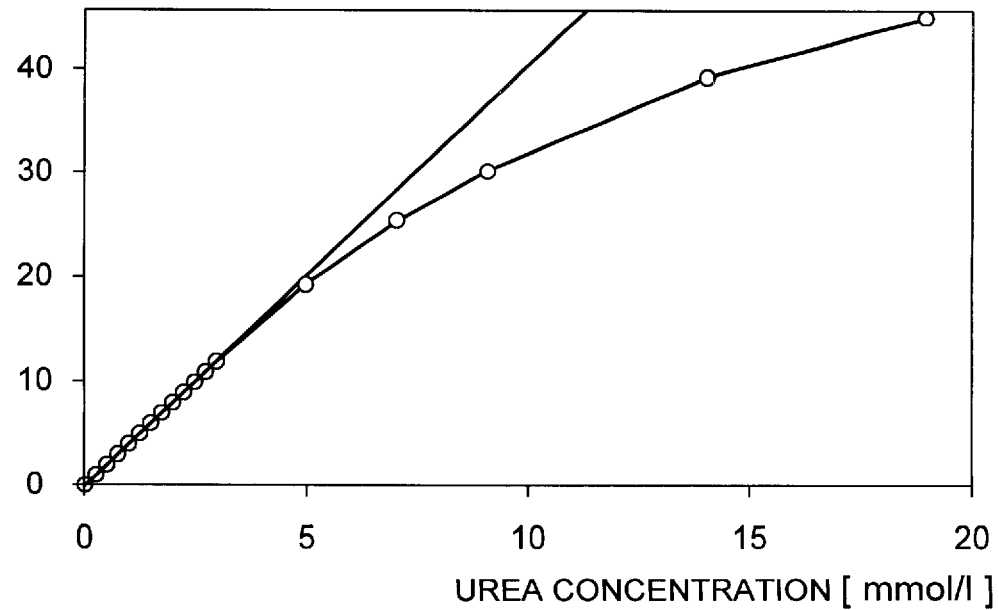
F I G. 5B

THICK-FILM CONDUCTIVITY ENZYME ELECTRODES IN A VERTICAL STACK AS BIOSENSOR

BACKGROUND OF THE INVENTION

1. Field of the Invention

The present invention is concerned with thick-film conductivity electrodes as biosensor, in particular with bioseneors for conductivity measurements of various analytes.

2. Brief Description of the Related Art

In recent years the development of biosensors in the field of research has been considerably advanced, and in particular, the use of biosensors has acquired increasing significance in the systematic detection of certain substances from a complex sample matrix. Biological molecules, such as, for example, enzymes, antibodies, nucleic acids or entire organisms, react in this connection specifically with the analyte to be detected. The parameters which alter during the reaction of the biological components with the analyte are transformed into recordable signals for signal processing by means of a transducer (for example, electrodes, field-effect transistors, photometers or glass-fibre optics).

Biosensors are often produced as immersion electrodes for single determinations. Biosensors have been known for a fairly long time as conductivity biosensors based on so-called thin-film electrodes. The materials of said thin-film electrodes are as a rule gold, platinum, palladium or alloys between these metals with silver. Said thin-film conductivity biosensors have the disadvantage that they have to be produced by a comparatively expensive technology which is very cost-intensive and consequently makes the biosensor itself too expensive for a wide-spread use. Furthermore, it is regarded as disadvantageous that the production of the transducer can not be carried out with the same technology as the deposition of an enzyme layer. In addition, an extreme miniaturisation is in many cases unnecessary and is; not always aimed at because of a better manageability of the sensors.

More recently, more and more different types of hick-film technology have been used for the production of conductive structures on a substrate, which is as a rule composed of ceramic. The thick-film technology is based on printing paste on a substrate by the screen-printing method and firing them. In this way, hybrid circuits can be produced, since the pastes have certain electronic properties (conductivity, capacitance). Recently, this technology has also been used for the production of sensors of the most varied type. For the production of biosensors, the electrochemical sensors are primarily of significance. Since there is a multiplicity of commercial pastes of very varied composition and conductivity, structures can be printed which can in principle be used as conventional noble-metal electrodes (gold, platinum, palladium and alloys between these metals with silver). These electrodes have the advantage that they have comparatively small dimensions which are typically approximately 50 $\mu$m for the line width and approximately 10 $\mu$m for the film thickness. These devices can be manufactured in an industrial process and are consequently available as a mass-produced product for the user.

Conductivity measurements or so-called admittance measurements are based on the measurement of the current as a function of an applied voltage, alternating voltage with a typical amplitude of 1 V and a frequency of 4 kHz being used as a rule. The conductivity Y of a solution is the reciprocal of the resistance R and consequently $$Y=I/U.$$

As a rule, it is represented as a complex variable:

$$Y=G+iB.$$

Here the real part G is the ohmic component, i.e. the component which is determined by the migration of charges in the electrical field. Added to this component are furthermore essentially capacitive components which are determined by the electrode/solution boundary layer and result in a phase shift between applied voltage and resultant current. They are referred to as susceptance B and represent the imaginary component of the admittance Y. Apart from these contributions, the measured value also depends on the area A and the spacing 1 of the electrodes used, which are combined in the cell constant as 1/A. Conventional conductivity measuring cells therefore contain two electrodes of defined area, which are at a definite spacing from one another. Conductivity electrodes can also form the basis of biosensors since, in a number of reactions which occur with a biological component, the conductivity alters at the location of the biological component. Since these biological components are as a rule immobilised on the electrodes, conductivity changes in the electrode/solution boundary layer are involved and not necessarily those which would also be measurable macroscopically as change in the entire solution.

As already mentioned above, the hitherto known thin-film methods for the production of biosensors are too expensive and therefore too cost-intensive.

It is therefore the object of the present invention to provide a conductivity biosensor which is simple and inexpensive in the production.

SUMMARY OF THE INVENTION

Accordingly, the method for the production of multidimensional conductivity biosensors on a substrate is characterised in that pastes are deposited by the screen-printing method on the substrate as thick-film conductivity electrodes of suitable materials and enzymes are immobilised on the thick-film conductivity electrodes.

BRIEF DESCRIPTION OF THE DRAWINGS

FIG. 5a shows the dependence of the admittance of the KC1 concentration which was obtained with the aid of a thick-film conductivity sensor with two-dimensional structure;

FIG. 5b shows a urea calibration curve which was measured with a thick-film conductivity sensor with two-dimensional structure and urease membrane;

DETAILED DESCRIPTION OF THE PREFERRED EMBODIMENTS OF THE INVENTION

Figure 2:
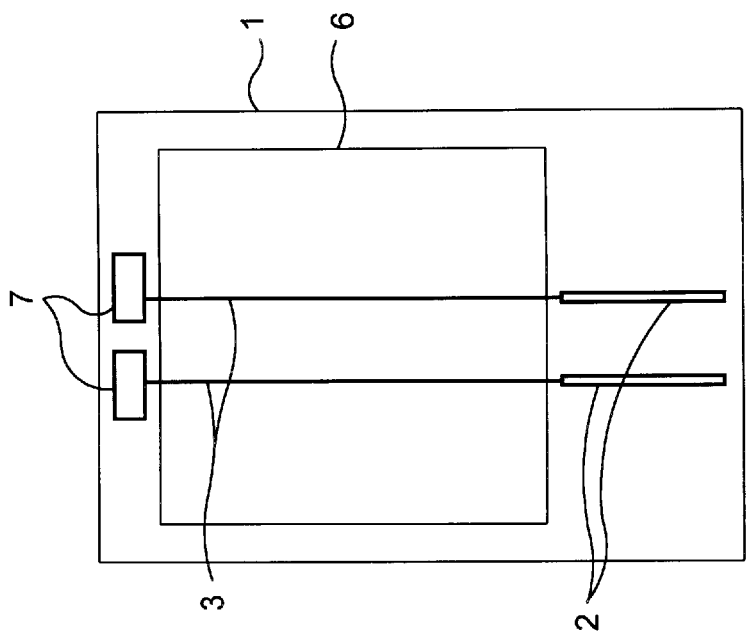
FIG. 2 shows a diagrammatic representation of a thick-film conductivity sensor as alternative layout to that from FIGS. 1.

With the biosensor presented here it has been shown that screen-printing methods are also suitable for the production of conductivity electrodes. With the aid of these methods, the same structures cad be produced as with thin-film methods. The thick-film technology has the decisive advantage that it is substantially more cost-effective than the previously known thin-film technology, which cannot be used in every run-of-the-mill factory.

In addition, it is advantageous that the production of the transducer can be carried out with the same technology as the deposition of the enzyme layer.

Various substrates and pastes can be used for the production of thick-film biosensors: the conventional thick-film process is based on pastes which, after printing and drying, are fired by a characteristic temperature programme, which is characterised by a peak temperature of 850° C. In this case, ceramics serve as substrates, but other materials can also be used in this process.

In addition to the conventional materials, such as gold or platinum, with which essentially two-dimensional structures can be built up, unfired ceramic has been introduced some years ago as substrate agent. This material has the advantage that here a plurality of layers can be pressed together and then fired, so that three-dimensional structures are effortlessly achievable. In addition, thick-film pastes were developed which can be cured at room temperature, so that plastics can also be used as substrate. With the appropriate pastes, all the substrates are suitable for the manufacture of conductivity biosensors.

For the production of two-dimensional structures, two electrodes are printed with a noble-metal paste on the substrate. Platinum and gold are primarily suitable as metals. The supply conductors can advantageously be printed with another conductive paste, which may contain, for example, silver and/or palladium. They are coated with an insulating paste.

According to the invention, an enzyme which catalyzes a reaction in which ions are formed from neutral molecules is immobilised on the conductivity electrodes deposited by thin-film technology. As examples, urease, penicillinase, esterases, hydrolases, amino acid oxidase and glucose oxidase may be mentioned. The immobilisation may be carried out by a method known from the literature, i.e. adsorption, occlusion in a matrix, crosslinking with bifunctional reagents or covalent binding to a carrier may be involved. The thick-film conductivity biosensor produced in this way can be used for the determination of the respective enzyme substrate or, alternatively, for the determination of the enzyme activity. Inhibitors or activators of enzymes can be detected via the measurement of the enzyme activity. Advantageously, three-dimensional structures can be produced with the aid of the unfired ceramic. That is to say, sensors with at least two electrodes or those with four electrodes in the case of so-called four-pole measurements or even multiple electrodes in the case of multiple sensors can be produced by variation of the number of printed layers.

Further advantageous developments are to be inferred from the subordinate claims and the description of the exemplary embodiments.

Figure 1:
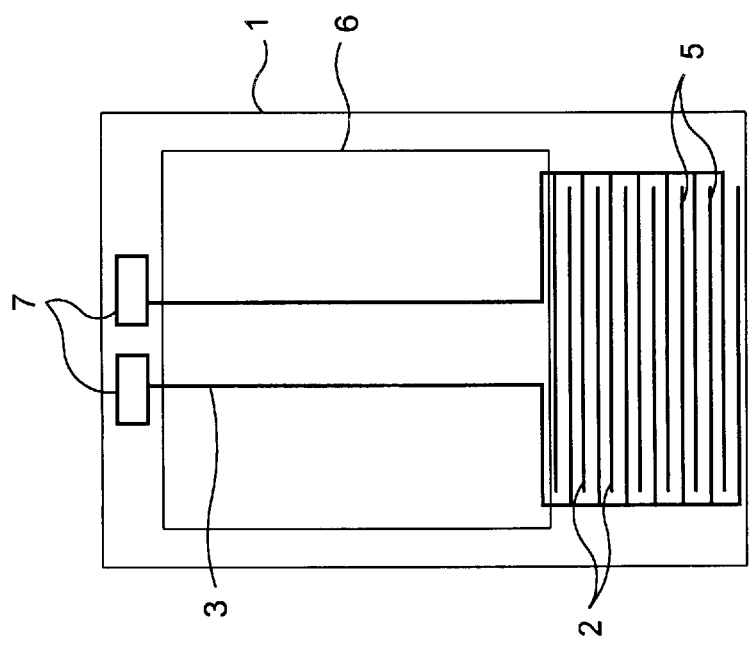
FIG. 1 shows a diagrammatic representation of a thick-film conductivity sensor with two-dimensional structure.

A possible layout of a substrate 1 is shown in FIG. 1. This is a comb-like structure of the thick-film conductivity electrodes 2 according to the invention which are disposed with a spacing of 300 $\mu$m and an electrode width of 500 $\mu$m. The total active electrode area is about 1.7 cm$^2$. It can, however, be varied without altering the result by altering the number of "teeth" 5 of the combs. Likewise, no alteration of the result occurs if the spacing or the width of the teeth 5 is altered. A layout with two parallel thick-film conductivity electrodes 2 according to the invention, as is to be inferred from FIG. 2, may be regarded as an extreme case of these modifications. Fundamentally different electrode arrangements are, however, also possible and can be used for the measurement of the conductivity. As an example, mention might furthermore be made of the arrangement of the thick-film conductivity electrodes 2 according to the invention in concentric circuits, as is shown in FIG. 3.

Resistance measurements are possible not only with two electrodes but also with four electrodes, i.e. In a so-called four-pole measurement, which is used in more than two-dimensional structures. Precisely these multidimensional structures are well suited to the biosensors according to the invention and are simple to produce.

Figure 3:
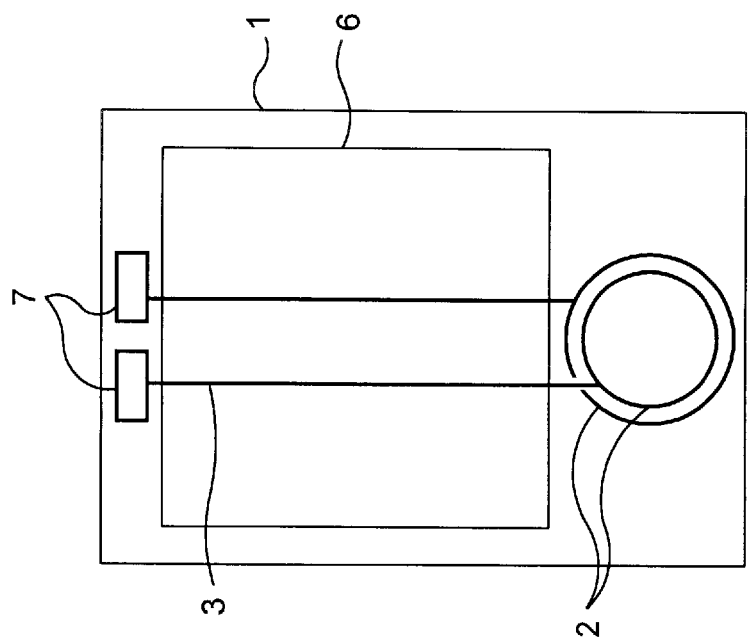
FIG. 3 shows a diagrammatic representation of a thick-film conductivity sensor as alternative layout to FIGS. 1 and 2.

Furthermore, the conductor tracks 3, which serve as current supply conductors for the conductivity measurement, are to be seen in FIGS. 1 to 3. These conductor tracks are routed over an insulating layer 6 which is deposited between the connections 7 and the actual thick-film conductivity electrodes on the substrate 1.

Figure 4:
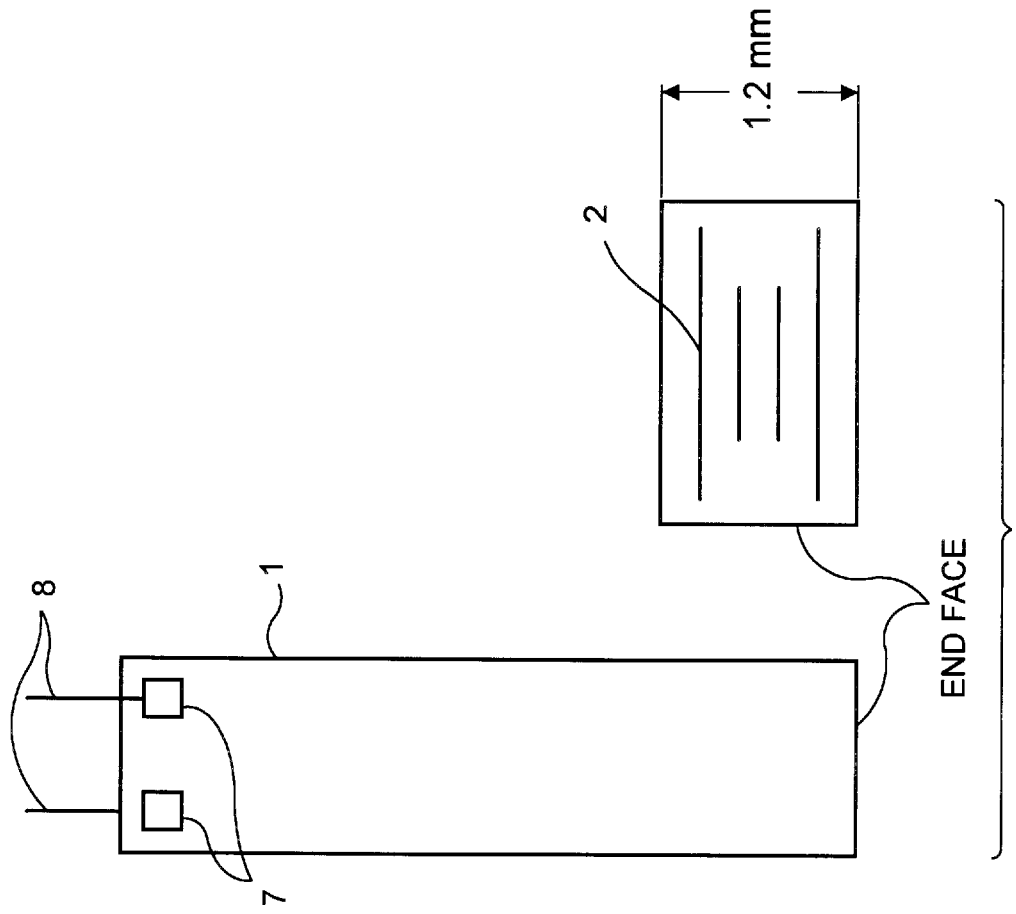
FIG. 4 shows a diagrammatic representation of a conductivity thick-film sensor with three-dimentional structure in side view and the view of the end face.

A diagrammatic representation of a thick-film sensor with three-dimensional structure is shown in FIG. 4. The figure furthermore shows the side view and the view of an end face of this three-dimensional thick-film sensor. Here the thick-film conductivity electrodes 2 are combined one on top of the other in a plurality of substrate layers, so that a height of the layers of 1.2 mm in total results. The take-off conductors 8 are each provided on a side face of the biosensor and, in particular, at the point where the connections 7 of the conductor tracks 3 are located.

Calibrations curves, which were obtained with the thick-film conductivity electrodes according to the invention, are shown in FIGS. 5a and 5b. In FIG. 5a, the admittance is plotted as a function of the KCl concentration with an alternating voltage frequency of 1 kHz and an amplitude of 100 mV. The suitability of these sensors for the determination of the conductivity of electrolyte solutions is consequently shown. For the determination of urea, the admittance Y was not plotted directly, but its rate of change (dY/dt) on adding urea to a urea-free solution.

In this way, the measurement duration can be appreciably shortened since it is not necessary to wait for any establishment of equilibrium. As a signal, peaks whose height is evaluated are typically obtained.

The peak height is plotted as a function of the urea concentration In FIG. 5b. This sensor was obtained from that of FIG. 5a. The biosensor for this measurement was of the same type as was used in FIG. 5a, but the enzyme urease was immobilised on the electrodes by crosslinking with the bifunctional reagent glutaraldehyde.

Urease catalyses the hydrolysis of urea:

Urea+3 H$_2$O - - - 2NH$_4^+$+HCO$_3^-$+OH$^-$

By suitable coupling of a plurality of enzymes on the electrodes, in addition to the abovementioned enzyme substrates, others are accessible to a measurement with conductivity electrodes, for example creatine can be determined by coupling creatinase and urease and creatinine can also be determined by coupling creatininase, creatinase and urease:

creatininase: creatinine+H$_2$O - - - creatine$^-$+H$^+$
creatine: creatine$^-$+H$_2$O - - - sarcosine$^2$+urea+H$^-$
urease: urea+3 H$_2$O - - - 2 NH$_4^+$+HCO$_3$H$^-$+OH$^-$ In this way, sensors for a plurality of analytes can be combined on one thick-film substrate.

A three-dimensional structure, such as is shown in FIG. 4, can be produced, for example, with the aid of the unfired ceramic. Sensors with at least two electrodes or more electrodes (multiple sensors) can be produced by variation of the number of printed layers.

As enzymes, the same ones as mentioned above, which are immobilised on the end face of the sensor, may be used. As methods for the immobilisation, the methods described in the literature are suitable, in particular the crosslinking of the enzyme with glutaraldehyde.

Figure 6:
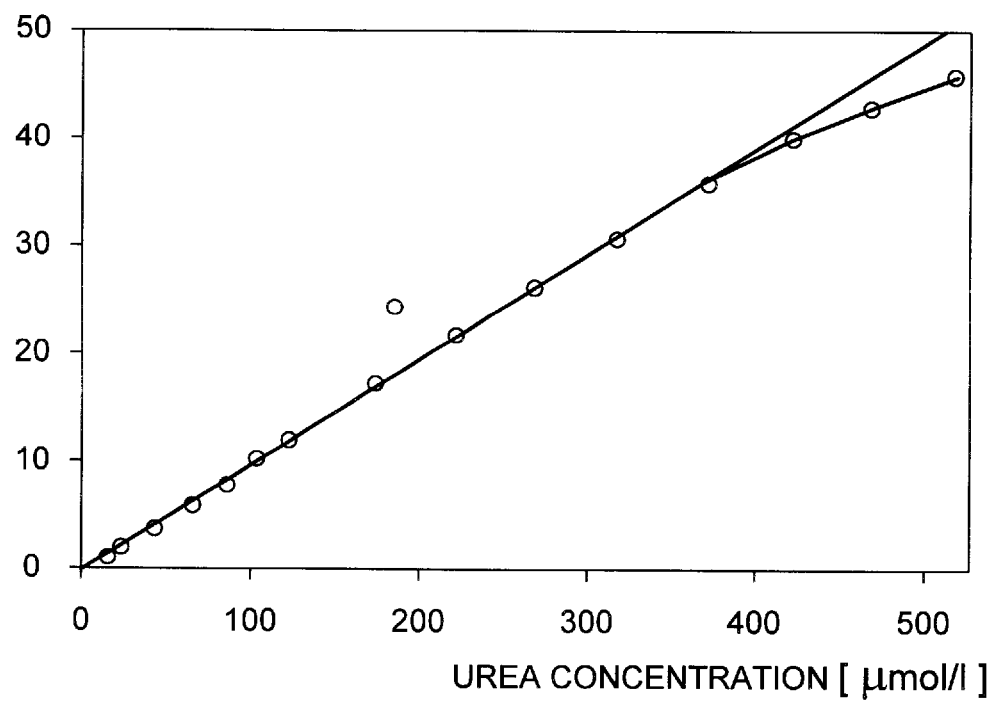
FIG. 6 shows a urea calibration curve which was measured with a thick-film conductivity sensor with three-dimensional structure and urease membrane.

FIG. 6 shows a calibration curve for urea as an example. The biosensor was produced by crosslinking urease with glutaraldehyde on a sensor with the design of FIG. 4. The measurements were carried out with an alternating voltage of 4 kHz and an amplitude of 1 V.

With the present invention it was consequently shown that it is possible to produce, with the so-called thick-film technology, biosensors which are, on the one hand, simpler in the production and, on the other hand, substantially more inexpensive.

We claim:

1. A method for the production of a conductivity biosensor which comprises;

a plurality of electrodes on a plurality of substrates; and an enzyme immobilized on the electrodes;

comprising the steps;

A. screen printing on a plurality of separate substrates a conductive electrode forming thick film paste, whereby the electrode is formed on the substrate;

B. immobilizing an enzyme on the electrode;

C. disposing the separate substrates bearing printed conductive electrodes and immobilized enzyme in a vertical stack, one on top of the other;

D. pressing the stacked substrates together; and

E. curing the printed paste, whereby a multi-dimensional biosensor is produced.

2. The method of claim 1 wherein the substrate is an unfired ceramic.

3. The method of claim 1 wherein the substrate is selected from the group consisting of a fired ceramic and a plastic.

4. The method of claim 1 wherein the paste is a noble metal paste.

5. The method of claim 1 wherein the enzyme is one which catalyzes a reaction wherein ions are released.

6. The method of claim 1 wherein a plurality of different enzymes are immobilized on different electrodes.

7. The method of claim 1 wherein immobilization is by cross-linking with a bifunctional reagent.

8. A conductivity biosensor, which comprises;

A. a plurality of substrate layers pressed together in a vertical stack;

B. each substrate layer bearing a conductive electrode formed thereon by screen printing a thick film paste; and C. each electrode having immobilized thereon an enzyme for sensing an analyte.

9. The biosensor of claim 8 wherein the electrodes are positioned in different geometric forms.

10. The biosensor of claim 8 wherein the electrodes are printed as parallel lines.

11. The biosensor of claim 8 wherein the electrodes are printed in the image of a comb.

12. The biosensor of claim 8 wherein the electrodes are printed in the image of concentric circles.

13. The biosensor of claim 8 wherein immobilization is by cross-linking with a bifunctional reagent.

14. A conductivity biosensor for detecting the presence of a plurality of different analytes, which comprises;

A. a plurality of substrate layers pressed together in a vertical stack;

B. each substrate layer bearing on the surface thereof, a conductive electrode formed by a screen-printing of a thick-film paste of electrode forming composition;

C. each electrode having immobilized thereon an enzyme for sensing at least one of said analytes;

D. at least two of the electrodes having enzymes for detecting different analytes; and E. conductor means attached to the electrodes for supplying electrical current thereto.

\* \* \* \* \*